(12) United States Patent
Nabi et al.

(10) Patent No.: US 10,400,199 B2
(45) Date of Patent: Sep. 3, 2019

(54) CLEANSING BARS WITH TAURINE

(71) Applicant: Colgate-Palmolive Company, New York, NY (US)

(72) Inventors: Zeenat Nabi, Cranbury, NJ (US); Viktor Dubovoy, Cresskill, NJ (US); Jeffrey Mastrull, Flemington, NJ (US); Daniel Talancon, Mexico City (MX); Shujiang Cheng, Warren, NJ (US); Laurence Du-Thumm, Princeton, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/532,516

(22) PCT Filed: Dec. 5, 2014

(86) PCT No.: PCT/US2014/068796
§ 371 (c)(1),
(2) Date: Jun. 2, 2017

(87) PCT Pub. No.: WO2016/089422
PCT Pub. Date: Jun. 9, 2016

(65) Prior Publication Data
US 2017/0335251 A1    Nov. 23, 2017

(51) Int. Cl.
| | | |
|---|---|---|
| *C11D 17/00* | (2006.01) | |
| *C11D 9/32* | (2006.01) | |
| *A61K 8/31* | (2006.01) | |
| *A61K 8/46* | (2006.01) | |
| *A61Q 19/10* | (2006.01) | |
| *A61K 8/92* | (2006.01) | |
| *A61K 8/02* | (2006.01) | |
| *C11D 3/18* | (2006.01) | |
| *C11D 3/20* | (2006.01) | |
| *C11D 3/34* | (2006.01) | |
| *C11D 3/382* | (2006.01) | |
| *C11D 9/24* | (2006.01) | |
| *C11D 9/26* | (2006.01) | |
| *C11D 9/38* | (2006.01) | |

(52) U.S. Cl.
CPC .............. *C11D 9/32* (2013.01); *A61K 8/0216* (2013.01); *A61K 8/31* (2013.01); *A61K 8/466* (2013.01); *A61K 8/922* (2013.01); *A61Q 19/10* (2013.01); *C11D 3/18* (2013.01); *C11D 3/2013* (2013.01); *C11D 3/2079* (2013.01); *C11D 3/349* (2013.01); *C11D 3/382* (2013.01); *C11D 9/24* (2013.01); *C11D 9/26* (2013.01); *C11D 9/267* (2013.01); *C11D 9/38* (2013.01); *C11D 17/006* (2013.01); *A61K 2800/52* (2013.01)

(58) Field of Classification Search
CPC .................................................. C11D 17/0047
USPC ............................................................ 510/141
See application file for complete search history.

(56) References Cited

U.S. PATENT DOCUMENTS

| | | | |
|---|---|---|---|
| 2,880,219 A | 3/1959 | Burnette et al. | |
| 3,926,829 A | 12/1975 | Smith et al. | |
| 5,139,781 A | 8/1992 | Birtwistle et al. | |
| 6,248,703 B1 | 6/2001 | Finucane et al. | |
| 6,344,435 B1 | 2/2002 | Miyahara et al. | |
| 6,352,965 B1 * | 3/2002 | Saito | C11D 3/3707 510/141 |
| 6,383,999 B1 | 5/2002 | Coyle et al. | |
| 8,683,908 B1 | 4/2014 | Smith, III et al. | |
| 9,809,788 B2 | 11/2017 | Pan et al. | |
| 2011/0201681 A1 | 8/2011 | Scala | |
| 2013/0303503 A1 * | 11/2013 | Smith, III | A61K 8/36 514/188 |
| 2014/0378363 A1 * | 12/2014 | Thiessies | C11D 3/126 510/151 |
| 2016/0312161 A1 * | 10/2016 | Gu | C11D 9/32 |

FOREIGN PATENT DOCUMENTS

| | | |
|---|---|---|
| CN | 1177289 A | 3/1998 |
| CN | 1196777 C | 4/2005 |
| EP | 1057888 | 12/2000 |
| EP | 1552817 | 7/2005 |
| JP | 2001-172692 | 6/2001 |
| RU | 2191802 C2 | 10/2002 |
| WO | WO 2015/088489 | 6/2015 |

OTHER PUBLICATIONS

International Search Report and Written Opinion in International Application No. PCT/US2014/068796, dated Aug. 4, 2015.

* cited by examiner

*Primary Examiner* — Gregory E Webb

(57) ABSTRACT

A cleansing bar composition comprising at least one cleanser chosen from soap and surfactant; taurine, in free or salt form; and one or more hydrophobic stabilizing agents. The hydrophobic stabilizing agent prevents the crystallization of taurine on the surface of the cleansing bar. Also methods of making the cleansing bar to inhibit crystallization of taurine in a cleansing bar.

18 Claims, No Drawings

CLEANSING BARS WITH TAURINE

BACKGROUND OF THE INVENTION

Taurine (2-aminoethanesulfonic acid) is a natural organic acid present in many animal organisms. Taurine is essential to the healthy maintenance of skeletal muscle, cardiovascular function, and central nervous system function. It is also an anti-oxidant and it helps stabilize cellular membranes.

Over the last 15 years, taurine and taurine derivatives have been used in a variety of cosmetic and personal care compositions, including hair conditioners, moisturizers, cleansing products, shaving cream and after-shave compositions. Taurine is suspected to have anti-fibrotic properties and has been shown to protect hair follicles from damage caused by the transforming growth factor family of proteins. Taurine also helps maintain skin hydration, contributing to the healthy maintenance of the skin barrier, and helps reduce inflammation and/or irritation of the skin.

Most of the cosmetic and personal care products that contain taurine are non-solid compositions, such as gels, creams, lotions, and liquids. In attempting to formulate a solid cleansing bar composition containing taurine, the inventors have found that under normal aging conditions (e.g., dry room temperature aging), gritty solid particles or crystals of taurine precipitate out of the composition on its surface. This gives the cleansing bar an unwelcome abrasive feel. Consequently, there is a need for formulating cleansing soap bars that deliver the beneficial effects of taurine without undesirable precipitation of taurine on the surface.

BRIEF SUMMARY

The inventors have discovered that taurine can be stabilized in a solid cleansing bar composition by the inclusion of hydrophobic stabilizing agents.

In a first exemplary embodiment, the present disclosure provides a cleansing bar composition comprising:
a) at least one cleanser chosen from soap and surfactant;
b) taurine, in free or salt form; and
c) one or more hydrophobic stabilizing agents
wherein the composition is a solid cleansing bar.

In a second exemplary embodiment, the invention includes a method of inhibiting taurine crystallization in a cleansing bar comprising
a) combining taurine, in free or salt form, with a hydrophobic stabilizing agent to form a mixture;
b) adding the mixture to at least one cleanser chosen from soap and surfactant; and
c) forming a cleansing bar.

Also, a use of a hydrophobic stabilizing agent to prevent crystallization of taurine when taurine is incorporated into a bar soap. The use is with any composition described herein.

DETAILED DESCRIPTION

Unless otherwise specified, all percentages and amounts expressed herein and elsewhere in the specification should be understood to refer to percentages by weight. As used throughout, ranges are used as shorthand for describing each and every value that is within the range. Any value within the range can be selected as the terminus of the range.

As used herein, the term "cleansing bar" shall include bars for cleansing and personal hygiene use comprising a cleanser chosen from soap and surfactant. The cleansing bar may be a soap bar (soap is the cleanser), syndet (non-soap surfactant is the cleanser), or combar (a mixture of soap and surfactant).

The present disclosure provides cleansing bars containing one or more cleansing materials, taurine and one or more hydrophobic stabilizing agents.

In one exemplary embodiment, the present disclosure provides a cleansing bar composition (Composition 1) comprising:
a) one or more (e.g., at least one) cleanser components;
b) taurine, in free or salt form; and
c) one or more (e.g., at least one) hydrophobic stabilizing agents.

The present disclosure provides additional exemplary embodiments, including 1.1 Composition 1, wherein the taurine is in free form (i.e., 2-aminoethanesulfonic acid).

1.2 Composition 1, wherein the taurine is in salt form, for example in acid addition salt form (e.g., taurine hydrochloride, taurine sulfate, taurine acetate).

1.3 Composition 1, wherein the taurine is in salt form, for example, in base addition salt form, e.g. as an alkali metal salt, alkaline earth metal salt, or ammonium salt (e.g., sodium, potassium, lithium, calcium or magnesium salt, or ammonium or tetralkylammonium salt, e.g., tetrabutylammonium salt).

1.4 Any of Compositions 1 or 1.1-1.3, where the weight ratio of taurine to hydrophobic stabilizing agent is 1:4 to 4:1.

1.5 Any of Compositions 1 or 1.1-1.4, where the weight ratio of taurine to hydrophobic stabilizing agent is 1:2.

1.6 Any of Compositions 1 or 1.1-1.5, wherein the taurine in free or salt form comprises from 0.1% to 10% by weight of the composition, measured as the equivalent amount of taurine in free form, e.g., from 1% to 10%, or e.g., from 2% to 8%, or e.g., from 4% to 6%, or about 5%.

1.7 Any of Compositions 1 or 1.1-1.6, wherein the taurine in free or salt form comprises from 1% to 10% by weight of the composition, measured as the equivalent amount of taurine in free form.

1.8 Any of Compositions 1 or 1.1-1.7, wherein the taurine in free or salt form comprises from 2% to 8% by weight of the composition, measured as the equivalent amount of taurine in free form.

1.9 Any of Compositions 1 or 1.1-1.8, wherein the taurine in free or salt form comprises from 4% to 6% by weight of the composition, measured as the equivalent amount of taurine in free form.

1.10 Any of Compositions 1 or 1.1-1.9, wherein the taurine in free or salt form comprises about 5% by weight of the composition, measured as the equivalent amount of taurine in free form.

1.11 Any of Compositions 1 or 1.1-1.10, wherein the one or more cleanser components comprise a soap, for example, an alkali metal (e.g., sodium or potassium) or alkylammonium (e.g., mono-, di- or tri-ethanol ammonium) salt of a carboxylic acid.

1.12 Any of Compositions 1 or 1.1-1.11, wherein the one or more soap components comprise an alkali metal (e.g., sodium or potassium) or alkylammonium salt of a fatty acid, e.g., a C8-22 saturated or unsaturated fatty acid, preferably a C10-20 saturated or unsaturated fatty acid.

1.13 Any of Compositions 1 or 1.1-1.12, wherein the one or more soap components comprise an alkali metal salt (e.g., sodium or potassium) or alkylammonium salt of a C8-22 carboxylic acid.

1.14 Any of Compositions 1 or 1.1-1.13, wherein the one or more soap components comprise the alkali metal (e.g., sodium or potassium) or alkylammonium salts of the fatty acids present in a natural vegetable oil, e.g., palm kernel oil, palm oil, coconut oil, olive oil or laurel oil, or in tallow (rendered animal fat).

1.15 Any of Compositions 1 or 1.1-1.14, wherein the one or more soap components comprise the alkali metal salt (e.g., sodium or potassium) of palm oil or coconut oil.

1.16 Any of Compositions 1 or 1.1-1.15, wherein the one or more soap components comprise from about 30, 40, 50 or 60% by weight of the composition to about 70, 80, 85, 90 or 95% by weight of the composition.

1.17 Any of Compositions 1 or 1.1-1.16, wherein the one or more hydrophobic stabilizing agents comprise at least one material chosen from a material having a water solubility less than 1% by weight, petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid, a silicone, or a mineral oil.

1.18 Any of Compositions 1 or 1.1-1.17, wherein the one or more hydrophobic stabilizing agents comprise petrolatum (e.g., white petrolatum or snow white petrolatum), a vegetable oil (e.g., palm oil, palm kernel oil, coconut oil), a seed oil (e.g., jojoba oil or wax), or a combination thereof.

1.19 Any of Compositions 1 or 1.1-1.18, wherein the one or more hydrophobic stabilizing agents comprise petrolatum (e.g., white petrolatum or snow white petrolatum), or a vegetable oil (e.g., palm oil, palm kernel oil, coconut oil), or a combination thereof.

1.20 Any of Compositions 1 or 1.1-1.19, wherein the one or more hydrophobic stabilizing agents comprise petrolatum (e.g., white petrolatum or snow white petrolatum), or palm kernel oil, or a combination thereof.

1.21 Any of Compositions 1 or 1.1-1.20, wherein the one or more hydrophobic stabilizing agents comprise 0.1% to 10% by weight of the composition, e.g., from 1% to 10%, or e.g., from 2% to 8%, or e.g., from 4% to 6%, or about 5%.

1.22 Any of Compositions 1 or 1.1-1.21, wherein the one or more hydrophobic stabilizing agents comprise 2% to 8% by weight of the composition.

1.23 Any of Compositions 1 or 1.1-1.22, wherein the one or more hydrophobic stabilizing agents comprise 4% to 6% by weight of the composition.

1.24 Any of Compositions 1 or 1.1-1.23, wherein the one or more hydrophobic stabilizing agents comprise about 5% by weight of the composition.

1.25 Any of Compositions 1 or 1.1-1.24, further comprising an anionic surfactant, cationic surfactant, zwitterionic surfactant, amphoteric surfactant, nonionic surfactant, or a combination thereof.

1.26 Any of Compositions 1 or 1.1-1.25, further comprising inorganic salts, brighteners, perfumes, colorants, sequestering agents, opacifiers, pearlizers, chelating agents (e.g., EDTA), humectants (e.g., polyols, for example, glycerol), or any combination thereof.

1.27 Any of Compositions 1 or 1.1-1.26, wherein the hydrophobic stabilizing agent prevents the precipitation (e.g., crystallization) of taurine on the surface of the cleansing bar.

1.28 Any composition which is the product of the combination of ingredients as identified for Composition 1 or 1.1-1.27.

1.29 Any foregoing composition wherein the taurine and hydrophobic stabilizing agent are pre-mixed, e.g., prior to combination with the soap component, such that the surface of the taurine particles is coated by the hydrophobic stabilizing agent.

1.30 Any foregoing composition wherein the taurine is substantially coated by the hydrophobic stabilizing agent.

1.31 Any foregoing composition wherein taurine does not precipitate or crystallize on the surface of the cleansing bar during aging.

The inventors have discovered that taurine can be stabilized in cleansing bars by the addition of hydrophobic stabilizing agents. These agents prevent the precipitation (e.g., crystallization) of taurine on the surface of the cleansing bar as it ages. These agents include, but are not limited to, a material having a water solubility less than 1% by weight (solubility is measured at 25° C.), petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid, a silicone, or a mineral oil. Mineral oils and petrolatum are both complex mixtures of hydrocarbons. Vegetable oils and fats are mixtures of tri-glycerides, i.e., the tri-glycerol esters of fatty acids. Seed oils, such as jojoba oil, are mixtures of waxes, i.e., the esters of fatty acids with long chain alcohols.

In preparing the cleansing bars of the present disclosure, the taurine component can be pre-mixed with the hydrophobic stabilizing agent, e.g., encapsulated by the hydrophobic stabilizing agent, prior to blending with the other components of the cleansing bar composition. Alternatively, the taurine can blended into the other components of the cleansing bar composition, before or after the addition of the hydrophobic stabilizing agents. Preferably, the taurine and hydrophobic stabilizing agent are pre-mixed and processed to ensure coating of the surface area of the taurine particles by the hydrophobic stabilizing agent.

The cleansing bar of the present disclosure includes at least one cleanser component. In certain embodiments the cleanser component is a hydrophilic soap chip (e.g., "a base component"). The term "soap" or "soap chip" is used herein in its popular sense, i.e., the alkali metal or alkanol ammonium salts of aliphatic alkane or alkene monocarboxylic acids. Sodium, potassium, mono-, di- and tri-ethanol ammonium cations, or combinations thereof, are suitable for purposes of this invention. In general, sodium soaps are used in the compositions of the present disclosure, but from about 1% to about 25% of the soap may be ammonium, potassium, magnesium, calcium soaps or a mixture of these soaps.

The soap chips useful herein include, but are not limited to, the well known alkali metal salts of aliphatic (alkanoic or alkenoic) acids having about 8 to 22 carbon atoms, preferably 10 to 20 carbon atoms. These may be described as alkali metal carboxylates of alkanoic or alkenoic hydrocarbons having about 12 to about 22 carbon atoms. Soaps having the fatty acid distribution of common vegetable oils may be suitable, e.g., palm kernel oil, palm oil, coconut oil, olive oil or laurel oil, or the fatty acid distribution of tallow (rendered animal fat). The soap may comprise the fatty acid distribution of any combination of natural or synthetic fatty acid sources (e.g., any combination of natural animal or vegetable fats or oils, and/or individual fatty acids).

Any other surfactant can also be present in the soap chip which include but are not limited to sulfate, sulfonate alpha olefin sulfonates, isethionates such as SCI, N-alkyl or N-acyl taurates, sulfosuccinate, phosphates, glycinates, amphoteric surfactants such as betaines, sulfobetaines and the like and nonionic surfactants such as alkanolamide, alkylpolyglycosides and all those surfactants, in general, mentioned in U.S. Pat. No. 5,139,781, column 5, line 35 to column 11, line 46.

In one exemplary embodiment, the cleansing bar of this disclosure includes at least about 70% by weight of cleanser active compounds (e.g., soap active compounds).

In an alternate exemplary embodiment, the cleanser of the composition consists essentially of anionic surfactant, nonionic surfactants, amphoteric surfactants, cationic surfactants and mixtures thereof.

Optional ingredients can be present in the cleansing bar composition. Non-limiting examples include skin conditioning agents, moisturizing agents, fragrance, dyes and pigments, titanium dioxide, chelating agents such as EDTA, sunscreen active ingredients such as butyl methoxy benzoylmethane; antiaging compounds such as alpha hydroxy acids, beta hydroxy acids; antimicrobial materials such as triclocarban, triclosan and the like; preservatives such as hydantoins, imidazolines; polyols such as glycerol, sorbitol, propylene glycol and polyethylene glycols; particulate matter such as silica, talc, or calcium carbonate; antioxidants such as butylated hydroxytoluene (BHT); vitamins such as A, E, K and C; essential oils and extracts thereof such as rosewood and jojoba, particulate matter such as polyethylene beads, jojoba beads, lufa, or oat flour, and mixtures of any of the foregoing components.

In one embodiment the cleansing bar includes fragrance in an amount of 0.001% to 2% by weight of the composition.

In one embodiment the cleansing bar includes pearlizers, such as titanium dioxide, in an amount of 0.01% to 1% by weight.

In one embodiment the cleansing bar includes one or more pigments, such as chromium oxide green, in an amount of 0.001% to 1% by weight.

In one embodiment, the cleansing bar includes silica, or silicon dioxide, incorporated at a level of from about 0.1% to about 15%, preferable from about 1% to about 10%, more preferably from about 3% to about 7%. Silica is available in a variety of forms, including but not limited to, crystalline, amorphous, fumed, precipitated, gel, and colloidal forms.

In one embodiment, the cleansing bar includes free fatty acids to provide enhanced skin feel benefits, such as softer or smoother feeling skin. Suitable free fatty acids include those derived from tallow, coconut oil, palm oil and palm kernel oil.

In a second exemplary embodiment, the invention includes a method (Method 1) of inhibiting taurine precipitation (e.g., crystallization) on the surface of a cleansing bar, comprising
a) combining taurine, in free or salt form, with a hydrophobic stabilizing agent to form a mixture;
b) adding the mixture to at least one cleanser chosen from soap and surfactant; and
c) forming a cleansing bar The present disclosure provides additional exemplary embodiments, including
1.1 Method 1, wherein the taurine is in free form (i.e., 2-aminoethanesulfonic acid).
1.2 Method 1, wherein the taurine is in salt form, for example in acid addition salt form (e.g., taurine hydrochloride, taurine sulfate, taurine acetate).
1.3 Method 1, wherein the taurine is in salt form, for example as an alkali metal salt, alkaline earth metal salt, or ammonium salt (e.g., sodium, potassium, lithium, calcium or magnesium salt, or ammonium or tetralkylammonium salt, e.g., tetrabutylammonium salt).
1.4 Any of Methods 1 or 1.1-1.3, wherein the weight ratio of taurine to hydrophobic stabilizing agent is 1:4 to 4:1.
1.5 Any of Methods 1 or 1.1-1.4, wherein the weight ratio of taurine to hydrophobic stabilizing agent is 1:2.
1.6 Any of Method 1 or 1.1-1.5, wherein the taurine in free or salt form comprises from about 0.1% to about 10% by weight of the cleansing bar, measured as the equivalent amount of taurine in free form, e.g., from about 1% to about 10%, or e.g., from about 2% to about 8%, or e.g., from about 4% to about 6%0, or about 5%.
1.7 Any of Method 1 or 1.1-1.6, wherein the taurine in free or salt form comprises from 1% to 10% by weight of the composition, measured as the equivalent amount of taurine in free form.
1.8 Any of Method 1 or 1.1-1.7, wherein the taurine in free or salt form comprises from 2% to 8% by weight of the composition, measured as the equivalent amount of taurine in free form.
1.9 Any of Method 1 or 1.1-1.8, wherein the taurine in free or salt form comprises from 4% to 6% by weight of the composition, measured as the equivalent amount of taurine in free form.
1.10 Any of Method 1 or 1.1-1.9, wherein the taurine in free or salt form comprises about 5% by weight of the composition, measured as the equivalent amount of taurine in free form.
1.11 Any of Methods 1 or 1.1-1.10, wherein the one or more cleanser components comprise a soap, for example, an alkali metal (e.g., sodium or potassium) or alkylammonium (e.g., mono-, di- or tri-ethanol ammonium) salt of a carboxylic acid.
1.12 Any of Methods 1 or 1.1-1.11, wherein the one or more soap components comprise an alkali metal (e.g., sodium or potassium) or alkylammonium salt of a fatty acid, e.g., a C8-22 saturated or unsaturated fatty acid, preferably a C10-20 saturated or unsaturated fatty acid.
1.13 Any of Methods 1 or 1.1-1.12, wherein the one or more soap components comprise an alkali metal salt (e.g., sodium or potassium) or alkylammonium salt of a C8-22 carboxylic acid.
1.14 Any of Methods 1 or 1.1-1.13, wherein the one or more soap components comprise the alkali metal (e.g., sodium or potassium) or alkylammonium salts of the fatty acids present in a natural vegetable oil, e.g., palm kernel oil, palm oil, coconut oil, olive oil or laurel oil, or in tallow (rendered animal fat).
1.15 Any of Methods 1 or 1.1-1.14, wherein the one or more soap components comprise the alkali metal salt (e.g., sodium or potassium) of palm oil or coconut oil.
1.16 Any of Methods 1 or 1.1-1.15, wherein the one or more soap components comprise from about 30, 40, 50 or 60% by weight of the composition to about 70, 80, 85, 90 or 95% by weight of the composition.
1.17 Any of Methods 1 or 1.1-1.16, wherein the one or more hydrophobic stabilizing agents comprise at least one material chosen from a material having a water solubility less than 1% by weight, petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid, a silicone, or a mineral oil.

1.18 Any of Methods 1 or 1.1-1.17, wherein the one or more hydrophobic stabilizing agents comprise petrolatum (e.g., white petrolatum or snow white petrolatum), a vegetable oil (e.g., palm oil, palm kernel oil, coconut oil), a seed oil (e.g., jojoba oil or wax), or a combination thereof.

1.19 Any of Methods 1 or 1.1-1.18, wherein the one or more hydrophobic stabilizing agents comprise petrolatum (e.g., white petrolatum or snow white petrolatum), or a vegetable oil (e.g., palm oil, palm kernel oil, coconut oil), or a combination thereof.

1.20 Any of Methods 1 or 1.1-1.19, wherein the one or more hydrophobic stabilizing agents comprise petrolatum (e.g., white petrolatum or snow white petrolatum), or palm kernel oil, or a combination thereof.

1.21 Any of Methods 1 or 1.1-1.20, wherein the one or more hydrophobic stabilizing agents comprise about 0.1% to about 10% by weight of the cleansing bar, e.g., from about 1% to about 10%, or e.g., from about 2% to about 8%, or e.g., from about 4% to about 6%, or about 5%.

1.22 Any of Methods 1 or 1.1-1.21, wherein the one or more hydrophobic stabilizing agents comprise 2% to 8% by weight of the composition.

1.23 Any of Methods 1 or 1.1-1.22, wherein the one or more hydrophobic stabilizing agents comprise 4% to 6% by weight of the composition.

1.24 Any of Methods 1 or 1.1-1.23, wherein the one or more hydrophobic stabilizing agents comprise about 5% by weight of the composition.

1.25 Any of Methods 1 or 1.1-1.24, wherein the taurine and the hydrophobic stabilizing agent are pre-mixed together, e.g., wherein the taurine is in powder form and combined with the hydrophobic stabilizing agent prior to being combined with any aqueous or hydrophilic soap components.

1.26 Any of Methods 1 or 1.1-1.25, wherein the hydrophobic stabilizing agent is heated to or above its melting point before it is combined with the taurine.

1.27 Any of Methods 1 or 1.1-1.26, wherein the taurine is substantially coated by the hydrophobic stabilizing agent.

1.28 Any of Methods 1 or 1.1-1.27, wherein the pre-mixture of taurine with the hydrophobic stabilizing agent is then blended with soap chips, and any other optional components of the final cleansing bar composition.

1.29 Any of Methods 1 or 1.1-1.28, further comprising the step of adding additional optional ingredients to the blended taurine/hydrophobic stabilizing agent and soap mixture.

1.30 Any of Methods 1 or 1.1-1.29, further comprising the processing of the final composition to produce cleansing bars.

1.31 Any of Methods 1 or 1.1-1.30, wherein the product cleansing bars consist essentially of any one of Compositions 1 or 1.1-1.31.

1.32 A cleansing bar that is prepared according to any of Methods 1 or 1.1-1.31.

The cleansing bars of the present disclosure may be prepared by any of the techniques known to those skilled in the art, including both batch processes and continuous processes. The first step in the preparation of the cleansing bar is the preparation of the soap component. Techniques known to those skilled in the art may be used, such as the classic kettle boiling process or the modern continuous soap manufacturing process. For example, an appropriate fat, oil, or carboxylic acid, or mixture thereof, is first combined with a base (e.g., sodium or potassium hydroxide or carbonate) in the presence of water to form the soap component. The soap component can then be processed and purified to remove excess base and/or glycerol as needed, and formed into chips, pellets, noodles or other solid or semi-solid forms. Optional ingredients such as additional surfactants may also be added after the removal of excess base but before formation into chips, pellets or noodles. The soap component may then be ground up, suspended in water and combined with the taurine and hydrophobic stabilizing agent, as well as other optional additives. Preferably, the taurine and hydrophobic stabilizing agents are pre-mixed, with melting of the hydrophobic stabilizing agent, if necessary. The mixture is processed, as by stirring or grinding to promote an even coating of the taurine particles by the hydrophobic stabilizing agent. The resulting mixture is then blended, with heating if necessary, with the soap chips and any other desired ingredients. After blending, the final composition is then formed into the finished cleansing bar product.

The cleansing bar may be formed by the extrusion method, and may be of varying sizes and shapes such as ovoid or rectangular in shape with either a flat or curved profile as an overall appearance.

EXAMPLES

Exemplary embodiments of the present disclosure will be illustrated by reference to the following examples, which are included to exemplify, but not to limit the scope of the present invention.

Example 1: Analysis of Stabilization Effect 2.50 grams of taurine crystals are placed into a mortar and ground up with a pestle. 2.50 g of stabilizing agent is added: (a) palm kernel oil, (b) white petrolatum, or (c) water (as a control). The palm kernel oil and white petrolatum are melted at 60° C. prior to mixing with the taurine. The mixture is thoroughly mixed and ground. Separately, a soap slurry is prepared by grinding up super-fat soap chips to a fine powder and mixing with water in a 1:0.3 ratio by weight. 60 g of this soap slurry is added to each of the taurine/hydrophobic stabilizing agent mixtures, and each is mixed to homogeneity. A small portion of each mixture is then transferred to a syringe and squeezed out to form a "noodle" on a microscope slide.

The noodles on the microscope slides are aged for two weeks at room temperature before being viewed with an Olympus SZX10 stereo microscope and photomicrographs of the noodles of the three compositions are analyzed. The control composition, containing water in place of a hydrophobic stabilizing agent, has clear crystals on the surface of the noodles. In contrast, the composition containing palm kernel oil has substantially reduced levels of crystallization, while the composition containing petrolatum has no crystallization.

Example 2: Cleansing Bar Composition

Table 1 shows exemplary base compositions according to the present disclosure. Each base composition can be optionally combined with additional ingredients to formulate a final cleansing bar. For example, water, fragrances, fillers and other ingredients disclosed hereinabove can be added.

| Material | Range | Formula A | Formula B |
|---|---|---|---|
| Sodium Soap Chips | 80-99.8% | 98% | 90% |
| Taurine | 0.1-10% | 1% | 5% |
| Snow White Petrolatum | 0.1-10% | 1% | 5% |

What is claimed is:

1. A cleansing bar composition comprising:
   a) at least one cleanser chosen from soap and surfactant;
   b) taurine, in free or salt form; and
   c) one or more hydrophobic stabilizing agents
   wherein the composition is a solid cleansing bar, and wherein the taurine is substantially coated by the hydrophobic stabilizing agent.

2. The composition of claim 1, wherein the taurine is in free form.

3. The composition of claim 1, wherein the taurine is in salt form and is selected from the group consisting of taurine hydrochloride, taurine sulfate, taurine acetate, alkali metal salt of taurine, alkaline earth metal salt of taurine, or ammonium salt of taurine.

4. The composition of claim 1, wherein the weight ratio of taurine to hydrophobic stabilizing agent is 1:4 to 4:1.

5. The composition of claim 1, wherein the taurine is present in an amount of 0.1% to 10% by weight of the composition.

6. The composition of claim 1, wherein the one or more hydrophobic stabilizing agents comprise at least one material chosen from a material having a water solubility less than 1% by weight, petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid, a silicone, or a mineral oil.

7. The composition of claim 6, wherein the hydrophobic stabilizing agent comprises petrolatum, white petrolatum, snow white petrolatum or palm kernel oil.

8. The composition of claim 1, wherein the hydrophobic stabilizing agent comprises 0.1% to 10% by weight of the composition.

9. The composition of claim 1, wherein the hydrophobic stabilizing agent prevents crystallization of taurine on the surface of the cleansing bar.

10. The composition of claim 1, wherein the at least one cleanser comprises a soap, wherein the soap is an alkali metal or alkylammonium salt of a C8-C22 carboxylic acid.

11. A method of inhibiting taurine crystallization in a cleansing bar comprising
    a) combining taurine, in free or salt form, in a hydrophobic stabilizing agent to form a mixture, so that the taurine is substantially coated by the hydrophobic stabilizing agent;
    b) adding the mixture to at least one cleanser chosen from soap and surfactant; and
    c) forming a cleansing bar.

12. The method of claim 11, wherein the taurine is in free form.

13. The method of claim 11, wherein the taurine is in salt form and is selected from the group consisting of taurine hydrochloride, taurine sulfate, taurine acetate, alkali metal salt of taurine, alkaline earth metal salt of taurine, or ammonium salt of taurine.

14. The method of claim 11, wherein the weight ratio of taurine to hydrophobic stabilizing agent is 1:4 to 4:1.

15. The method of claim 11, wherein the taurine is present in an amount of 0.1% to 10% by weight of the composition.

16. The method of claim 11, wherein the hydrophobic stabilizing agent comprises petrolatum or palm kernel oil.

17. The method of claim 11, wherein the hydrophobic stabilizing agent prevents crystallization of taurine on the surface of the cleansing bar.

18. The method of claim 11, wherein the at least one cleanser is a soap, wherein the soap is an alkali metal or alkylammonium salt of a C8-C22 carboxylic acid.

* * * * *